United States Patent [19]

Bringhurst et al.

[11] Plant 4,481

[45] Nov. 13, 1979

[54] STRAWBERRY PLANT

[75] Inventors: Royce S. Bringhurst, Davis; Victor Voth, Santa Ana, both of Calif.

[73] Assignee: The Regents of the University of California, Berkeley, Calif.

[21] Appl. No.: 953,992

[22] Filed: Oct. 23, 1978

[51] Int. Cl.[2] ..... A01H 5/03

[52] U.S. Cl. ..... Plt./49

[58] Field of Search ..... Plt./49

*Primary Examiner*—Robert E. Bagwill

*Attorney, Agent, or Firm*—Townsend and Townsend

[57] ABSTRACT

A new and distinct variety of strawberry plant of a short-day type characterized by its yield throughout California, equal to or greater than the heaviest yielding California cultivars. The plants are vigorous and prolific runner makers. The variety is particularly characterized by fruit which is hollow centered and medium conic and a high percentage which is wedgy flat ranging to coxcomb. Fruit is larger in size than that of Tufts, Tioga or Aiko and has flavor equal to or better than the best of the important California cultivars. Shipping qualities are adequate if fruit is harvested carefully.

2 Drawing Figures

This invention relates to a new and distinctive short-day type strawberry cultivar designated as "C55" which is the result of a cross between Cal 63.7-101 (not patented) and Cal 64.57-108 (not patented.)

C55 first fruited at the Wolfskill Experimental Orchards of the University of California near Davis in 1974, where it was selected and designated originally as Cal 72.361-105.

C55 has since been tested with favorable results and asexually reproduced by runners at various University of California Field Stations and facilities and has also been favorably tested in a limited way, in growers' fields under strict control. Meristem originated virus negative stock for asexual reproduction is under development at the University of California.

FIG. 1 of the accompanying photographic color reproduction shows typical growth, flowering and fruiting characteristics of C55 in a winter planting at Watsonville at mid-season.

Figure 1:
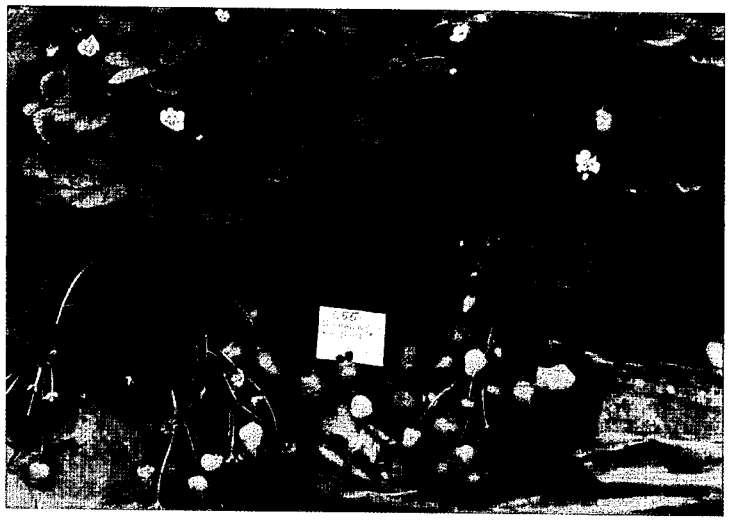
Figure 2:
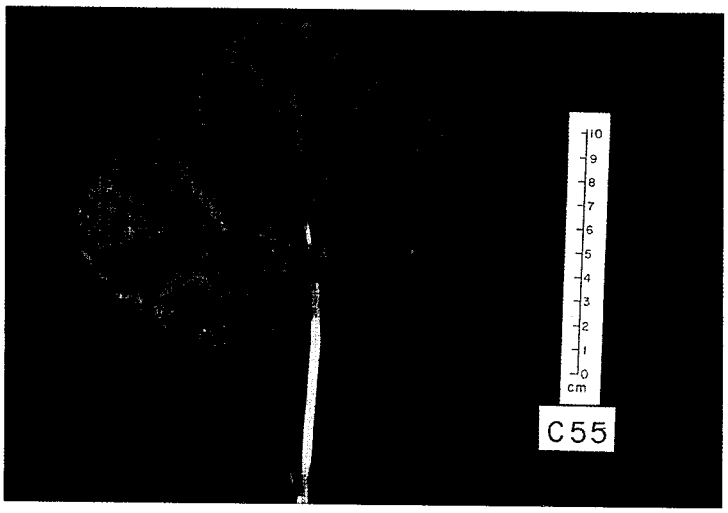
FIG. 2 shows a typical mid-summer mature leaf from a winter planted plant.
Figure 3:
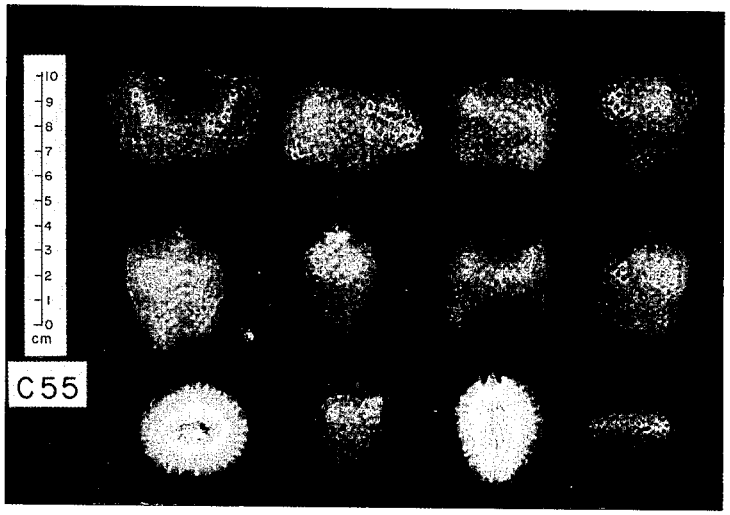
FIG. 3 shows a typical mid-season fruit of C55 with longitudinal and cross section views.

C55 has yielded well throughout California but has performed best in coastal, Central California where the mid to late summer crop of large, attractive fruit has been outstanding in appearance. The plants tend to get too large on summer plantings and winter plantings may prove more desirable. Yield trials have demonstrated that it is capable of yielding as much or more than the heavy yielding California cultivars "Aiko" (U.S. Plant Pat. No. 3,981), "Tioga" (not patented) and "Tufts" (U.S. Plant Pat. No. 3,561).

The distinctive characteristics of this new strawberry cultivar described in detail below were observed upon its discovery and/or through the test period.

DESCRIPTION

Plants and foliage. — C55 plants are erect in growth habit, somewhat similar to "Aiko" or "Tufts" but much larger than the former. Bract leaves occur on about 10% of the petioles of winter planted plants but seldom if ever on summer planted ones; much less than "Tioga", "Tufts" or "Aiko". Leaflets of C55 are about the same size as those of "Tioga", "Tufts" or "Aiko". Leaflets of C55 are about the same size as those of "Tioga"

or "Tufts", larger than "Aiko" and are lighter in color and slightly less yellow than those of "Tioga" but darker than those of "Tufts", about 5 GY 5/6 vs. 2.5 GY 4/3 and 7.5 GY 5/7, respectively (Munsell Color System—Nickerson Color Fan). The leaflets have almost as many serrations as those of "Tufts" (av of ±11/half blade vs. ±12 for "Tufts") more than those for "Tioga" or "Aiko" (av of ±10/half blade) as averaged over the half blades of leaves on mid-season mature plants at Watsonville. The plants are very vigorous and C55 is a prolific runner maker in the nursery. C55 tends to runner much less than "Tufts" in fruit plantings.

Isozymes in leaf extracts. — Phosphoglucose isomerase (PGI): C55 gave the slow 3 banded pattern similar to that of "Tufts", 30/35, 35/35, 35/35, 35/35 mm, different than the "Tioga" single band pattern or the "Aiko" 5 banded pattern (Scandalios. 1969. Biochem. Genet. 3:27–79).

Flowering and flowers. — C55 is a standard short-day type that commences heavy flowering later than "Tioga" and "Tufts" but earlier than "Aiko" in winter plantings. Inflorescences are long, comparable to those of "Tufts" but longer than those of "Aiko" and "Tioga". The plant tends to flower recurrently throughout the summer and into the fall, similar to "Aiko". The flowers are highly self fertile with ample pollen throughout the season.

Fruit and fruiting. — C55 has hollow centered medium conic fruit with a high percentage of wedgy, flat fruit ranging to large coxcomb. Much of the fruit has a small neck. The skin color of C55 is very similar to that of "Tioga", about 7.5 R 4.5/11 vs. 7.5 R 4.5/13 (ibid) for "Tioga". The finish is very glossy and the flesh color is very similar to that of the skin, except for a distinctly lighter area near the core. The calyx is large and particularly attractive with much of it semi reflexed. The achenes are positioned about flush with the surface, similar to "Tioga". The fruit is less firm and less durable than that of "Aiko", "Tioga" or "Tufts", although penetrometer readings are frequently about as high. C55 fruit must be picked on a more frequent schedule than is necessary for the above California cultivars. C55 fruit has averaged larger than that of "Tufts", "Tioga" or "Aiko", 23 vs. 21, 18 and 18 g/fr, respectively, in a Watsonville experiment.

Fruit quality. — Ascorbic acid: C55 averaged ±51 mg/100 g of fresh fruit, greater than that of "Tioga", (±40) or "Tufts" (±45) and less than "Aiko" (±60) as tested by the method of Loeffler and Ponting. 1942. J. Ind. and Eng. Chem. 14:846. Soluble solids: C55 averaged ±9.1%, not significantly different from "Aiko", "Tioga" or "Tufts" according to our measurements on mid-summer Watsonville fruit. The flavor of C55 is equal to or better than that of the best of the important California cultivars in our opinion. C55 may be adequate as a shipping fruit if it is harvested carefully on a frequent schedule and should be useful for processing.

We claim:

1. The new and distinct variety of strawberry plant herein described and illustrated, and identified by the characteristics enumerated above.

* * * * *